United States Patent [19]
Doyle, Jr. et al.

[11] 3,932,437
[45] Jan. 13, 1976

[54] MULTISTEP SYNTHESIS FOR CERTAIN 1,3,4-THIADIAZOLES AND INTERMEDIATE

[75] Inventors: William C. Doyle, Jr., Leawood; Loren W. Hedrich, Overland Park, both of Kans.

[73] Assignee: Gulf Research & Development Company, Pittsburgh, Pa.

[22] Filed: Aug. 13, 1973

[21] Appl. No.: 387,839

Related U.S. Application Data

[60] Division of Ser. No. 177,178, Sept. 1, 1971, Pat. No. 3,824,247, which is a continuation-in-part of Ser. No. 119,417, Feb. 26, 1971.

[52] U.S. Cl. .................. 260/306.8 D; 260/247.1 M
[51] Int. Cl.² ..................................... C07D 277/52
[58] Field of Search ............. 260/306.8 D, 247.1 M

[56] References Cited
UNITED STATES PATENTS

| | | | |
|---|---|---|---|
| 2,744,907 | 5/1956 | Young | 260/306.8 D |
| 3,033,901 | 5/1972 | Song | 260/306.8 D |
| 3,726,892 | 4/1973 | Cebalo | 260/306.8 D |

FOREIGN PATENTS OR APPLICATIONS

| | | | |
|---|---|---|---|
| 2,209,010 | 8/1972 | Germany | 260/306.8 D |

OTHER PUBLICATIONS

Wagner et al., Synthetic Organic Chemistry, N.Y.C., John Wiley & Sons, 1953, pp. 645, 647 and 821–823.

*Primary Examiner*—R. Gallagher

[57] ABSTRACT

The industrial herbicide 5-(1,3,3-trimethylureido)-N,N-dimethyl-1,3,4-thiadiazole-2-sulfonamide and other compounds of similar structure may be made by a novel procedure in which the first step is the oxidative chlorination of a 2-alkylamino-5-mercapto-1,3,4-thiadiazole to yield the corresponding sulfonyl chloride. The subject compound which possesses five methyl substituent groups is more effective as a herbicide than compounds which contain other alkyl substituents or a lesser number of methyl substituents.

3 Claims, No Drawings

MULTISTEP SYNTHESIS FOR CERTAIN 1,3,4-THIADIAZOLES AND INTERMEDIATE

This application is a division of application Ser. No. 177,178 filed Sept. 1, 1971, now U.S. Pat. No. 3,824,247, which is a continuation-in-part of application Ser. No. 119,417 filed Feb. 26, 1971. The disclosure of Ser. No. 119.417 is incorporated herein by reference.

DESCRIPTION OF THE INVENTION

U.S. Ser. No. 119,417 which is incorporated herein by reference discloses a new class of highly phytotoxic substances which may be applied to the locus of unwanted vegetation to effect control, either pre- or post-emergently. Effective compounds have the structural formula:

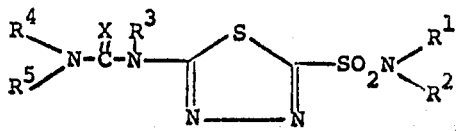

in which $R^1$ and $R^2$ are selected from hydrogen, lower cycloalkyl, lower alkyl, alkoxy, cyanoalkyl, aralkyl, alkoxyalkyl, alkylaminoalkyl, lower alkenyl and lower alkynyl substutients and heterocyclic structures in which $R^1$ and $R^2$ are together alkylene or oxyalkylene with two to five carbon atoms, $R^3$ is hydrogen, methyl or ethyl, $R^4$ is hydrogen or lower alkyl, $R^5$ is selected from lower alkyl, lower alkenyl and lower cycloalkyl substituents and X is oxygen or sulfur.

In the aforementioned application many specific compounds of the class are disclosed having a high degree of phytotoxicity and varied selectivity. It has been discovered that one of the compounds of this class, 5-(1,3,3-trimethylureido)-N,N-dimethyl-1,3,4-thiadiazole-2-sulfonamide, is an unusually effective herbicide of the type which is used industrially to prevent growth of weeds in railroad right-of-ways and in other areas where uncontrolled growth of vegetation is undesirable. In the aforementioned application, methods of synthesis of the new herbicides are also disclosed. A new, more direct method of synthesis of this class of herbicides has been discovered in which it has been found unnecessary to protect a free amino substitutent on the thiadiazole nucleus during oxidative chlorination. The method of synthesis of the class of herbicides and use of a superior member of the class to control a large number of species of plant life are specifically exemplified below.

Herbicide Synthesis

On the basis of disclosures in the chemical literature, particularly Roblin and Clapp, [J. Am. Chem. Soc. 72 4890 (1950)], the presence of a free amine function on the thiadiazole molecule precludes the conversion of the mercapto group to the corresponding sulfonyl chloride by oxidative chlorination. Oxidative chlorination is a well known technique, most conveniently operated by introducing chlorine into dilute aqueous hydrochloric acid reaction medium at room temperature or below, with the substance to be chlorinated present in solution or suspension. (See, for example, the publication by Petrow et al J. Chem. Soc. 1958, p. 1508). Amines are known to interfere with the reaction. Consequently a preferred approach to synthesis of the desired class of compounds has involved protection of the free amine group prior to oxidative chlorination, as shown below in the synthesis scheme which was disclosed in U.S. Ser. No. 119,417:

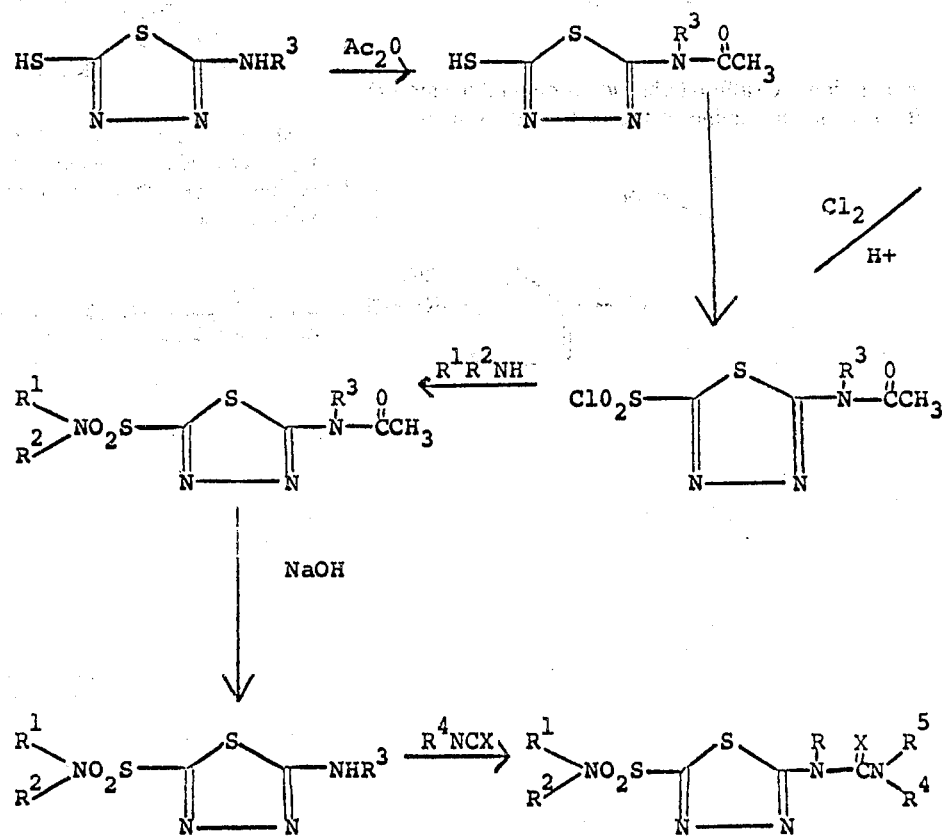

or

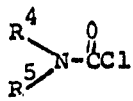

X = O, S

We have discovered, however, that protection of the amino substituent on the thiadiazole nucleus is unnecessary in the formation of the corresponding sulfonyl chloride by oxidative chlorination of the mercapto substituent. As a result of this discovery, herbicides of this class have now been synthesized by means of a more convenient and direct method, which consists of the following steps performed in sequence:

a. Chlorinating under oxidizing conditions an amine having the structural formula

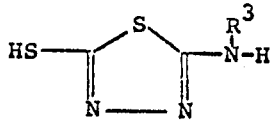

in which $R^3$ may be methyl or ethyl to yield a corresponding sulfonyl chloride having the structural formula

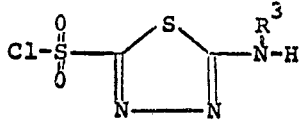

b. reacting the sulfonyl chloride produced in step (a) with a secondary amine of the structural formula

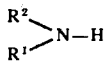

in which $R^1$ may be hydrogen or lower alkyl and $R^2$ may be hydrogen or lower alkyl or $R^1$ and $R^2$ together form a ring with the nitrogen atom to yield a sulfonamide having the structural formula

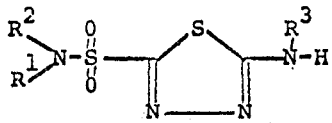

c. reacting the sulfonamide produced in step (b) with a carbamyl chloride or isocyanate having one of the structural formulae

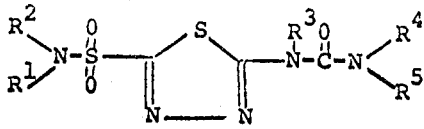

or
  $R^4$NCO or preferably reacting the amine substituent with phosgene in inert solvent followed by reacting the resulting carbamyl chloride with an amine having the structural formula

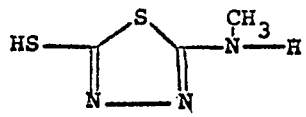

in which $R^4$ may be lower alkyl, preferably methyl and $R^5$ may be hydrogen or lower alkyl to yield a phytotoxic ureidothiadiazolesulfonamide having the structural formula:

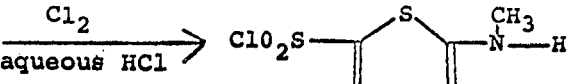

More specifically, the route to a superior industrial type herbicide composition is shown in the following scheme, in which alternate methods of carbamylation are outlined.

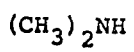

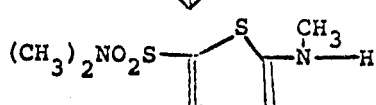

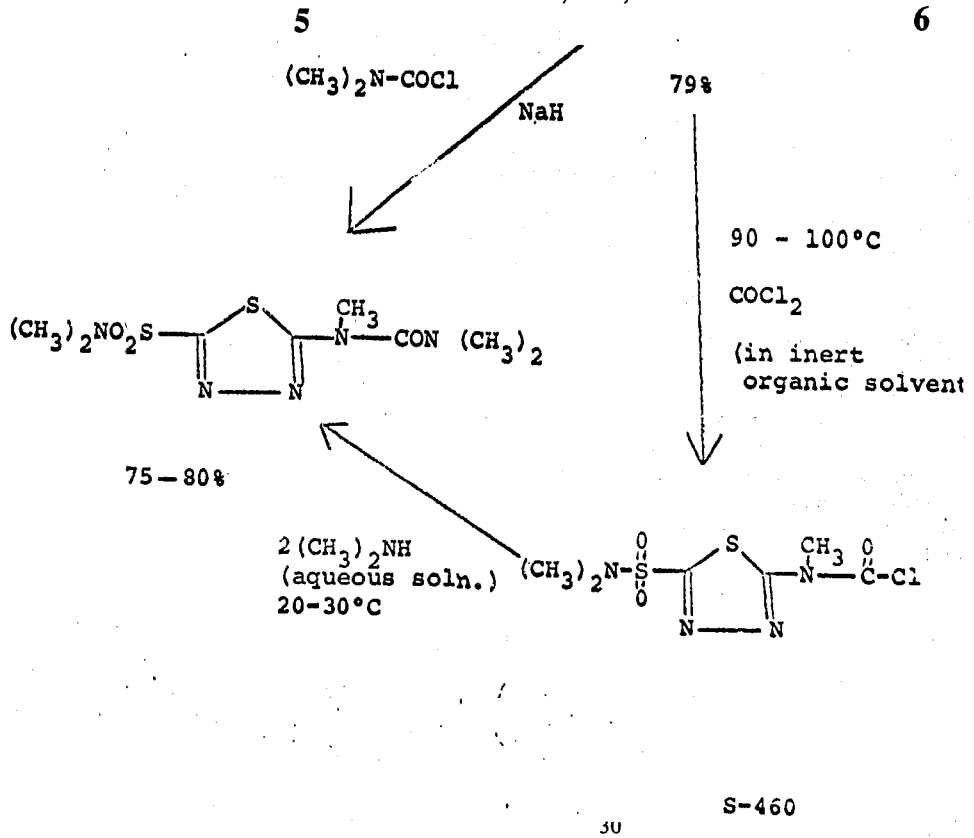

S-460

The synthesis of this compound is specifically exemplified as follows:

PREPARATION OF 2-METHYLAMINO-5-CHLOROSULFONYL-1,3,4-THIADIAZOLE

A rapid stream of chlorine is passed into a well stirred slurry of 55.0 g (0.374 mols) of 2-methylamino-5-mercapto-1,3,4-thiadiazole in 1,800 ml of 10% hydrochloric acid. While maintaining the temperature at 0° to (−10°) by cooling in an ice-salt bath, the chlorine addition is continued until no more chlorine is absorbed and the reaction mixture has a definite yellow color. Filtration of the solid and thorough washing with water gives 71.2 g of 2-methylamino-5-chlorosulfonyl-1,3,4-thiadiazole, m.p. 87° (dec.).

| Analysis: | Calc'd. | Found |
|---|---|---|
| | C 31.80 | 31.59 |
| | H 4.58 | 4.45 |
| | N 21.19 | 21.44 |

PREPARATION OF 2-METHYLAMINO-1,3,4-THIADIAZOLE-5-N,N-DIMETHYLSULFONAMIDE

To a solution of 24.0 g (0.133 mols) of 25% aqueous dimethylamine in 70 ml dioxane is added slowly 2-methylamino-5-chlorosulfonyl-1,3,4-thiadiazole (the damp filter cake from oxidative chlorination of 9.5 g, 0.0645 mols, of 2-methylamino-5-mercapto-1,3,4-thiadiazole) while stirring in an ice bath. After an additional 1 to 2 hours stirring, the mixture is diluted 3- to 4-fold with water, filtered and the crystalline product washed with water. The 2-methylamino-1,3,4-thiadiazole-5-N,N-dimethylsulfonamide (70% overall yield from I) melts at 168°–70°.

| Analysis: | Calc'd | Found |
|---|---|---|
| | C 27.00 | 26.79 |
| | H 4.50 | 4.51 |
| | N 25.25 | 25.13 |

PREPARATION OF 2-ETHYLAMINO-1,3,4-THIADIAZOLE-5-N-ETHYLSULFONAMIDE

Repeating the above procedure and reacting the damp filter cake (the dry product is unstable) from oxidative chlorination of 25.0 g of 2-ethylamino-5-mercapto-1,3,4-thiadiazole with 19.0 g of 70% aqueous ethylamine in 100 ml of dioxane gave 17.9 g of 2-ethylamino-1,3,4-thiadiazole-5-N-ethylsulfonamide, m.p. 137°–9°.

PREPARATION OF 2-(1,1,3-TRIMETHYLUREIDO)-1,3,4-THIADIAZOLE-5-N,N-DIMETHYLSULFONAMIDE

To a solution of 42.0 g (0.19 mols) of 2-methylamino-1,3,4-thiadiazole-5-N,N-dimethylsulfonamide in 225 ml of dimethylformamide is added, with ice-bath cooling, 10.2 g of a 57% oil dispersion of sodium hydroxide. After stirring 30 minutes at room temperature 20.4 g (0.19 mole) of N,N-dimethylcarbamyl chloride is added slowly, without cooling, with the reaction temperature rising to about 55°. The mixture is then heated to 90° for 3 hours, vacuum stripped, and the residue partitioned between benzene and water. The benzene layer is separated, evaporated and the residue is triturated with hexane to give 43 g of 2-(1,1,3-trimethylureido)-1,3,4-thiadiazole-5-N,N-dimethylsulfonamide, m.p. 103°–5°.

The following method, based on simple, cheap raw materials is preferred for conversion of the amino-substituted thiadiazolesulfonamide to the corresponding ureido substituted compound.

REACTION OF 2-METHYLAMINO-1,3,4-THIADIAZOLE-5-N,N-DIMETHYLSULFONAMIDE WITH PHOSGENE AND DIMETHYLAMINE

Phosgene is bubbled into a well stirred slurry of 10.0 g of 2-methylamino-1,3,4-thiadiazole-5-N,N-dimethylsulfonamide and 100 ml of dry toluene heated to 90°–100°. The solid starting material slowly dissolves and the phosgene addition is continued 30 minutes after a clear solution results. While maintaininig the temperature at 90°–100° a rapid stream of nitrogen is passed through the solution for 1 hour to remove the excess phosgene. The toluene solution is filtered to remove a trace of gummy precipitate, cooled to 20°–25° and 12.0 g of 40% aqueous dimethylamine is added slowly, keeping the temperature below 30°. The mixture is then heated to 50°–60° for 30 minutes, cooled, washed with two 100 ml portions of water and the toluene is removed under vacuum. The crystalline residue is slurried with hexane and filtered to give 10.0 g (76% yield) of 2-(1,3-dimethylureido)-1,3,4-thiadiazole-5-N,N-dimethylsulfonamide, m.p. 101°–5°.

Carrying out the reaction in the same way, except that the 2-methylamin-1,3,4-thiadiazole-5-N,N-dimethylsulfonamide was first converted to the hydrochloride in a stream of anhydrous hydrogen chloride gave a 78% yield of product, m.p. 101°–2°.

Specific compounds which are illustrative of the class of herbicides which may be manufactured by the improved method of this invention are listed in Table I.

Combating Unwanted Vegetation

The novel herbicides are effective when used both post- and pre-emergently. There is described below an illustrative procedure for herbicidal use of the compounds under controlled conditions in the greenhouse so as to obtain data on phytotoxic activity and selectivity.

1. Post-Emergent Use

An aqueous dispersion of each active compound was prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The 24 species of plants on which each compound was to be tested were planted in disposable plastic pots in a greenhouse. Ten to 18 days after emergence of the plants, three pots of each species were sprayed at each rate with an aqueous dispersion of the active compound prepared as described above, at rates of both 1 lb and 3 lb of active compound per acre and at a spray volume of 60 gallons per acre. Approximately 1 week after the spray application the plants were observed and the results rated according to the following schedule.

DEGREE OF EFFECT

| | |
|---|---|
| 0 = | no effect |
| 1 = | slight effect |
| 2 = | moderate effect |
| 3 = | severe effect |
| 4 = | maximum effect (all plants died) |

The same rating schedule was employed to judge pre-emergent results obtained according to the procedure below.

2. Pre-Emergent Use

A solution of each active compound was prepared by dissolving 290 mg of the compound to be tested in 200 ml of acetone. Disposable paper trays about 2 ½ inches deep were filled with soil and sprayed with the acetone solution at rates of 3 lb and 1 lb of active chemical per acre of sprayed area, were seeded with 24 species of plant seeds and were then covered with about ¼ inch of soil. Twenty-one days after seeding and treatment the plantings were examined and herbicidal effect was rated according to the above schedule.

Both post-emergent and pre-emergent results are set forth in Table II. Compound No. 1 did not show a significant herbicidal effect in the pre-emergence test and no data are given. Compound No. 11 did not show a significant effect in either the pre- or post-emergence tests at either 1 lb or 3 lb per acre.

TABLE I

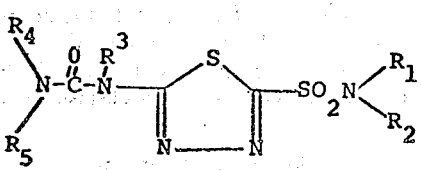

| Compound | No. of CH₃ Groups | R¹ | R² | R³ | R⁴ | R⁵ | Melting Point °C |
|---|---|---|---|---|---|---|---|
| No. 1 | 1 | H | H | H | H | CH₃ | >310 |
| 2 | 2 | H | CH₃ | H | H | CH₃ | 227–228 |
| 3 | 3 | H | CH₃ | CH₃ | H | CH₃ | 158–160 |
| 4 | 3 | CH₃ | CH₃ | H | H | CH₃ | 193–196 |
| 5 | 4 | CH₃ | CH₃ | CH₃ | H | CH₃ | 211–214 |
| 6 | 5 | CH₃ | CH₃ | CH₃ | CH₃ | CH₃ | 103–105 |
| 7 | 0 | C₂H₅ | C₂H₅ | C₂H₅ | C₂H₅ | C₂H₅ | (Liquid) b.p. 203–205°/0.3mm hg |
| 8 | 1 | H | CH₂=CHCH₂ | H | H | CH₃ | 193–194.5 |
| 9 | 1 | H | n-C₄H₉ | H | H | CH₃ | 183–185 |
| 10 | 1 | H | t-C₄H₉ | H | H | CH₃ | 245–246 (decomp.) |
| 11 | 3 | CH₃O | CH₃ | CH₃ | H | CH₃ | 216.5–217 |
| 12 | 1 | —CH₂CH₃ | OCH₂CH₂— | H | H | CH₃ | 229–230 |

TABLE II

COMPOUND NO. 1

| MODE OF APPLICATION | POST 3 lb/A | 1 lb/A |
|---|---|---|
| Plant Species | | |
| Cocklebur | 1 | 0 |
| Lambsquarter | 1 | 0 |
| Morning Glory | 1 | 0 |
| Pigweed | 1 | 0 |
| Wild Buckwheat | 2 | 0 |
| Wild Mustard | 1 | 0 |
| Barnyard Grass | 0 | 0 |
| Crabgrass | 0 | 0 |
| Downy Brome | 0 | 0 |
| Giant Foxtail | 0 | 0 |
| Green Foxtail | 0 | 0 |
| Nutsedge | 0 | 0 |
| Shattercane | 0 | 0 |
| Wild Oats | 0 | 0 |
| Alfalfa | 0 | 0 |
| Cotton | 1 | 0 |
| Peanut | 0 | 0 |
| Soybean | 1 | 0 |
| Sugar Beets | 1 | 0 |
| Tomato | 1 | 0 |
| Corn | 0 | 0 |
| Grain Sorghum | 0 | 0 |
| Rice | 0 | 0 |
| Wheat | 0 | 0 |

COMPOUND NO. 2

| MODE OF APPLICATION | PRE 3 lb/A | 1 lb/A | POST 3 lb/A | 1 lb/A |
|---|---|---|---|---|
| Plant Species | | | | |
| Cocklebur | 0 | 0 | × | × |
| Lambsquarter | 4 | 1 | 4 | 4 |
| Morning Glory | 0 | 0 | 1 | 1 |
| Pigweed | 4 | 3 | 4 | 4 |
| Wild Buckwheat | 2 | 0 | 4 | 4 |
| Wild Mustard | 4 | 1 | 4 | 4 |
| Barnyard Grass | 4 | 3 | 4 | 4 |
| Crabgrass | 4 | 3 | 4 | 4 |
| Downy Brome | 3 | 0 | 3 | 1 |
| Giant Foxtail | 4 | 2 | 4 | 4 |
| Green Foxtail | 4 | 2 | 4 | 4 |
| Nutsedge | 0 | 0 | 0 | 0 |
| Shattercane | 4 | 3 | 4 | 3 |
| Wild Oats | 3 | 1 | 4 | 4 |
| Alfalfa | 3 | 1 | 4 | 4 |
| Cotton | 0 | 0 | 4 | 4 |
| Peanut | 0 | 0 | 2 | 1 |
| Soybean | 0 | 0 | 4 | 2 |
| Sugar Beets | 1 | 0 | 4 | 4 |
| Tomato | 4 | 1 | 4 | 4 |
| Corn | 3 | 2 | 2 | 1 |
| Grain Sorghum | 4 | 2 | 4 | 3 |
| Rice | 4 | 3 | 4 | 3 |
| Wheat | 4 | 3 | 4 | 4 |

COMPOUND NO. 3

| MODE OF APPLICATION | PRE 3 lb/A | 1 lb/A | POST 3 lb/A | 1 lb/A |
|---|---|---|---|---|
| Plant Species | | | | |
| Cocklebur | 4 | 4 | 4 | 3 |
| Lambsquarter | 4 | 4 | 4 | 4 |
| Morning Glory | 4 | 4 | 4 | 4 |
| Pigweed | 4 | 4 | 4 | 4 |
| Wild Buckwheat | 4 | 4 | 4 | 4 |
| Wild Mustard | 4 | 4 | 4 | 4 |
| Barnyard Grass | 4 | 4 | 4 | 2 |
| Crabgrass | 4 | 4 | 4 | 3 |
| Downy Brome | 4 | 4 | 4 | 1 |
| Giant Foxtail | 4 | 4 | 4 | 2 |
| Green Foxtail | 4 | 3 | 4 | 3 |
| Nutsedge | 3 | 0 | 0 | 0 |
| Shattercane | 4 | 4 | 4 | 1 |
| Wild Oats | 4 | 4 | 4 | 3 |
| Alfalfa | 4 | 3 | 4 | 4 |
| Cotton | 4 | 3 | 4 | 4 |
| Peanut | 3 | 1 | 4 | 2 |
| Soybean | 4 | 4 | 4 | 4 |
| Sugar Beets | 4 | 4 | 4 | 4 |
| Tomato | 4 | 4 | 4 | 4 |
| Corn | 4 | 2 | 1 | 0 |
| Grain Sorghum | 4 | 4 | 2 | 1 |
| Rice | 4 | 4 | 4 | 2 |
| Wheat | 4 | 4 | 4 | 3 |

COMPOUND NO. 4

| MODE OF APPLICATION | PRE 3 lb/A | 1 lb/A | POST 3 lb/A | 1 lb/A |
|---|---|---|---|---|
| Plant Species | | | | |
| Cocklebur | 4 | 1 | 4 | 4 |
| Lambsquarter | 4 | 4 | 4 | 4 |
| Morning Glory | 4 | 0 | 4 | 4 |
| Pigweed | 4 | 4 | 4 | 1 |
| Wild Buckwheat | 4 | 1 | 4 | 4 |
| Wild Mustard | 4 | 4 | 4 | 4 |
| Barnyard Grass | 4 | 4 | 4 | 4 |
| Crabgrass | 4 | 4 | 4 | 4 |
| Downy Brome | 4 | 4 | 4 | 1 |
| Giant Foxtail | 4 | 4 | 4 | 4 |
| Green Foxtail | 4 | 4 | 4 | 4 |
| Nutsedge | 3 | 0 | 0 | 0 |
| Shattercane | 4 | 4 | 4 | 1 |
| Wild Oats | 4 | 4 | 4 | 2 |
| Alfalfa | 4 | 4 | 4 | 4 |
| Cotton | 4 | 1 | 4 | 3 |
| Peanut | 2 | 0 | 3 | 1 |
| Soybean | 4 | 4 | 3 | 1 |
| Sugar Beets | 4 | 4 | 4 | 4 |
| Tomato | 4 | 4 | 4 | 4 |
| Corn | 4 | 4 | 1 | 0 |
| Grain Sorghum | 4 | 4 | 3 | 1 |
| Rice | 4 | 4 | 4 | 2 |
| Wheat | 4 | 4 | 4 | 2 |

COMPOUND NO. 5

| MODE OF APPLICATION | PRE 3 lb/A | 1 lb/A | POST 3 lb/A | 1 lb/A |
|---|---|---|---|---|
| Plant Species | | | | |
| Cocklebur | 4 | 4 | 3 | 1 |
| Lambsquarter | 4 | 4 | 4 | 4 |
| Morning Glory | 4 | 4 | 4 | 4 |
| Pigweed | 4 | 4 | 4 | 4 |
| Wild Buckwheat | 4 | 4 | 4 | 4 |
| Wild Mustard | 4 | 4 | 4 | 4 |
| Barnyard Grass | 4 | 4 | 4 | 3 |
| Crabgrass | 4 | 4 | 4 | 4 |
| Downy Brome | 4 | 4 | 4 | 1 |
| Giant Foxtail | 4 | 4 | 4 | 2 |
| Green Foxtail | 4 | 4 | 4 | 4 |
| Nutsedge | 4 | 2 | 0 | 0 |
| Shattercane | 4 | 4 | 4 | 1 |
| Wild Oats | 4 | 4 | 4 | 4 |
| Alfalfa | 4 | 4 | 4 | 4 |
| Cotton | 4 | 4 | 4 | 4 |
| Peanut | 4 | 3 | 3 | 1 |
| Soybean | 4 | 4 | 4 | 4 |
| Sugar Beets | 4 | 4 | 4 | 4 |
| Tomato | 4 | 4 | 4 | 4 |
| Corn | 4 | 4 | 3 | 0 |
| Grain Sorghum | 4 | 4 | 3 | 0 |
| Rice | 4 | 4 | 4 | 4 |
| Wheat | 4 | 4 | 4 | 4 |

COMPOUND NO. 6

| MODE OF APPLICATION | PRE 3 lb/A | 1 lb/A | POST 3 lb/A | 1 lb/A |
|---|---|---|---|---|
| Plant Species | | | | |
| Cocklebur | 4 | 4 | 4 | 4 |
| Lambsquarter | 4 | 4 | 4 | 4 |
| Morning Glory | 4 | 4 | 4 | 4 |
| Pigweed | 4 | 4 | 4 | 4 |
| Wild Buckwheat | 4 | 4 | 4 | 4 |
| Wild Mustard | 4 | 4 | 4 | 4 |
| Barnyard Grass | 4 | 4 | 4 | 3 |
| Crabgrass | 4 | 4 | 4 | 2 |
| Downy Brome | 4 | 4 | 4 | 4 |
| Giant Foxtail | 4 | 4 | 4 | 3 |
| Green Foxtail | 4 | 4 | 4 | 4 |
| Nutsedge | 3* | 3* | 2 | 0 |
| Shattercane | 4 | 4 | 4 | 3 |
| Wild Oats | 4 | 4 | 4 | 4 |
| Alfalfa | 4 | 4 | 4 | 4 |
| Cotton | 4 | 4 | 4 | 4 |
| Peanut | 4 | 3 | 4 | 4 |
| Soybean | 4 | 4 | 4 | 4 |
| Sugar Beets | 4 | 4 | 4 | 4 |
| Tomato | 4 | 4 | 4 | 4 |
| Corn | 4 | 4 | 4 | 3 |
| Grain Sorghum | 4 | 4 | 4 | 3 |
| Rice | 4 | 4 | 4 | 4 |
| Wheat | 4 | 4 | 4 | 4 |

COMPOUND NO. 7

| MODE OF APPLICATION | PRE 3 lb/A | 1 lb/A | POST 3 lb/A | 1 lb/A |
|---|---|---|---|---|
| Plant Species | | | | |
| Cocklebur | 0 | 0 | 0 | 0 |
| Lambsquarter | 3 | 3 | 2 | 0 |
| Morning Glory | 1 | 0 | 1 | 0 |
| Pigweed | 4 | 3 | 0 | 0 |
| Wild Buckwheat | 1 | 0 | 1 | 0 |

TABLE II-continued

COMPOUND NO. 1

| MODE OF APPLICATION | POST 3 lb/A | 1 lb/A | | |
|---|---|---|---|---|
| Wild Mustard | 3 | 3 | 2 | 0 |
| Barnyard Grass | 2 | 0 | 0 | 0 |
| Crabgrass | 4 | 1 | 0 | 0 |
| Downy Brome | 1 | 0 | 0 | 0 |
| Giant Foxtail | 1 | 0 | 0 | 0 |
| Green Foxtail | 0 | 0 | 0 | 0 |
| Nutsedge | 0 | 0 | 0 | 0 |
| Shattercane | 0 | 0 | 0 | 0 |
| Wild Oats | 1 | 0 | 0 | 0 |
| Alfalfa | 1 | 0 | 1 | 0 |
| Cotton | 0 | 0 | 1 | 0 |
| Peanut | 0 | 0 | 0 | 0 |
| Soybean | 0 | 0 | 1 | 0 |
| Sugar Beets | 3 | 1 | 1 | 0 |
| Tomato | 3 | 1 | 1 | 0 |
| Corn | 0 | 0 | 0 | 0 |
| Grain Sorghum | 0 | 0 | 0 | 0 |
| Rice | 0 | 0 | 0 | 0 |
| Wheat | 1 | 0 | 0 | 0 |

COMPOUND NO. 8

| MODE OF APPLICATION | PRE 3 lb/A | 1 lb/A | POST 3 lb/A | 1 lb/A |
|---|---|---|---|---|
| Plant Species | | | | |
| Cocklebur | x | x | x | x |
| Lambsquarter | 4 | 4 | 4 | 4 |
| Morning Glory | 0 | 0 | 1 | 1 |
| Pigweed | 4 | 4 | 4 | 4 |
| Wild Buckwheat | 2 | 1 | 4 | 4 |
| Wild Mustard | 3 | 0 | 4 | 4 |
| Barnyard Grass | 4 | 3 | 4 | 1 |
| Crabgrass | 4 | 3 | 4 | 3 |
| Downy Brome | 4 | 3 | 3 | 1 |
| Giant Foxtail | 4 | 3 | 4 | 2 |
| Green Foxtail | 3 | 1 | 4 | 1 |
| Nutsedge | 0 | 0 | 0 | 0 |
| Shattercane | 3 | 1 | 2 | 0 |
| Wild Oats | 4 | 2 | 3 | 1 |
| Alfalfa | 1 | 0 | 3 | 2 |
| Cotton | 0 | 0 | 3 | 1 |
| Peanut | 0 | 0 | 1 | 0 |
| Soybean | 2 | 0 | 2 | 2 |
| Sugar Beets | 4 | 1 | 4 | 3 |
| Tomato | 4 | 3 | 4 | 4 |
| Corn | 4 | 1 | 2 | 1 |
| Grain Sorghum | 3 | 1 | 2 | 0 |
| Rice | 4 | 3 | 3 | 1 |
| Wheat | 4 | 4 | 3 | 1 |

COMPOUND NO. 9

| MODE OF APPLICATION | PRE 3 lb/A | 1 lb/A | POST 3 lb/A | 1 lb/A |
|---|---|---|---|---|
| Plant Species | | | | |
| Cocklebur | x | x | x | x |
| Lambsquarter | 4 | 4 | 4 | 4 |
| Morning Glory | 0 | 0 | 2 | 1 |
| Pigweed | 4 | 4 | 4 | 4 |
| Wild Buckwheat | 1 | 0 | 4 | 3 |
| Wild Mustard | 4 | 0 | 4 | 4 |
| Barnyard Grass | 3 | 2 | 3 | 3 |
| Crabgrass | 3 | 3 | 4 | 3 |
| Downy Brome | 3 | 1 | 2 | 1 |
| Giant Foxtail | 3 | 2 | 3 | 2 |
| Green Foxtail | 2 | 1 | 4 | 2 |
| Nutsedge | 0 | 0 | 0 | 0 |
| Shattercane | 1 | 0 | 2 | 0 |
| Wild Oats | 3 | 2 | 3 | 1 |
| Alfalfa | 1 | 0 | 4 | 3 |
| Cotton | 0 | 0 | 3 | 0 |
| Peanut | 0 | 0 | 1 | 0 |
| Soybean | 1 | 0 | 3 | 3 |
| Sugar Beets | 4 | 1 | 4 | 3 |
| Tomato | 4 | 0 | 4 | 4 |
| Corn | 1 | 0 | 2 | 0 |
| Grain Sorghum | 1 | 0 | 2 | 0 |
| Rice | 3 | 2 | 2 | 1 |
| Wheat | 4 | 3 | 2 | 1 |

COMPOUND NO. 10

| MODE OF APPLICATION | PRE 3 lb/A | 1 lb/A | POST 3 lb/A | 1 lb/A |
|---|---|---|---|---|
| Plant Species | | | | |
| Cocklebur | x | x | x | x |
| Lambsquarter | 3 | 1 | 1 | 0 |
| Morning Glory | 0 | 0 | 0 | 0 |
| Pigweed | 4 | 2 | 1 | 0 |
| Wild Buckwheat | 0 | 0 | 1 | 0 |
| Wild Mustard | 0 | 0 | 2 | 0 |
| Barnyard Grass | 2 | 0 | 0 | 0 |
| Crabgrass | 3 | 0 | 0 | 0 |
| Downy Brome | 1 | 0 | 0 | 0 |
| Giant Foxtail | 2 | 0 | 0 | 0 |
| Green Foxtail | 1 | 0 | 0 | 0 |
| Nutsedge | 0 | 0 | 0 | 0 |
| Shattercane | 0 | 0 | 0 | 0 |
| Wild Oats | 0 | 0 | 0 | 0 |
| Alfalfa | 0 | 0 | 0 | 0 |
| Cotton | 0 | 0 | 0 | 0 |
| Peanut | 0 | 0 | 0 | 0 |
| Soybean | 0 | 0 | 1 | 1 |
| Sugar Beets | 4 | 0 | 2 | 1 |
| Tomato | 1 | 1 | 2 | 1 |
| Corn | 0 | 0 | 0 | 0 |
| Grain Sorghum | 0 | 0 | 0 | 0 |
| Rice | 1 | 0 | 0 | 0 |
| Wheat | 1 | 0 | 0 | 0 |

COMPOUND NO. 12

| MODE OF APPLICATION | PRE 3 lb/A | 1 lb/A | POST 3 lb/A | 1 lb/A |
|---|---|---|---|---|
| Plant Species | | | | |
| Cocklebur | 0 | 0 | 2 | 1 |
| Lambsquarter | 4 | 4 | 4 | 3 |
| Morning Glory | 1 | 0 | 2 | 1 |
| Pigweed | 4 | 4 | 4 | 4 |
| Wild Buckwheat | 0 | 0 | 4 | 3 |
| Wild Mustard | 1 | 0 | 4 | 3 |
| Barnyard Grass | 4 | 3 | 2 | 0 |
| Crabgrass | 4 | 1 | 4 | 1 |
| Downy Brome | 4 | 0 | 2 | 0 |
| Giant Foxtail | 4 | 1 | 3 | 0 |
| Green Foxtail | 4 | 4 | 4 | 3 |
| Nutsedge | 0 | 0 | 0 | 0 |
| Shattercane | 4 | 2 | 0 | 0 |
| Wild Oats | 4 | 4 | 1 | 0 |
| Alfalfa | 4 | 4 | 4 | 4 |
| Cotton | 1 | 0 | 4 | 4 |
| Peanut | 0 | 0 | 1 | 1 |
| Soybean | 0 | 0 | 3 | 1 |
| Sugar Beets | 4 | 1 | 4 | 4 |
| Tomato | 4 | 3 | 4 | 4 |
| Corn | 2 | 1 | 0 | 0 |
| Grain Sorghum | 4 | 2 | 0 | 0 |
| Rice | 4 | 4 | 1 | 0 |
| Wheat | 4 | 4 | 2 | 1 |

0= no injury
4= complete kill
*- all plants died in about 1 to 2 additional weeks The relative effectiveness of 12 compounds having various combinations of substituents on 24 plant species was summarized by adding the scores at both application levels of 1 pound per acre and 3 pounds per acre and comparing the totals. The comparative results appear in the following table from which it is clearly apparent that the compound 5-(1,3,3-trimethylureido)-N,N-dimethyl-1,3,4-thiadiazole-2-sulfonamide out-performed all of the compounds which contained a lesser number of methyl substituent groups.

TABLE III

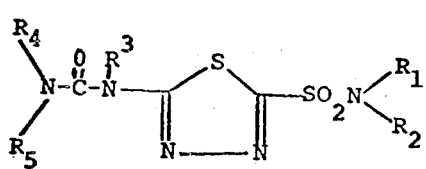

TABLE III

| Compound | No. of CH₃ Groups | R¹ | R² | R³ | R⁴ | R⁵ | PRE Σ3 lb/A | PRE Σ1 lb/A | POST Σ3 lb/A | POST Σ1 lb/A | Σ(Total) |
|---|---|---|---|---|---|---|---|---|---|---|---|
| No. 1 | 1 | H | H | H | H | CH₃ | — | — | 11 | 0 | 11 |
| 2 | 2 | H | CH₃ | H | H | CH₃ | 63 | 31 | 80 | 71 | 245 |
| 3 | 3 | H | CH₃ | CH₃ | H | CH₃ | 94 | 84 | 87 | 66 | 331 |
| 4 | 3 | CH₃ | CH₃ | H | H | CH₃ | 93 | 75 | 86 | 63 | 317 |
| 5 | 4 | CH₃ | CH₃ | CH₃ | H | CH₃ | 96 | 93 | 88 | 69 | 346 |
| 6 | 5 | CH₃ | CH₃ | CH₃ | CH₃ | CH₃ | 95 | 94 | 94 | 89 | 372 |
| 7 | 0 | C₂H₅ | C₂H₅ | C₂H₅ | C₂H₅ | C₂H₅ | 29 | 12 | 11 | 0 | 52 |
| 8 | 1 | H | CH₂=CHCH₂ | H | H | CH₃ | 65 | 38 | 68 | 41 | 212 |
| 9 | 1 | H | n-C₄H₉ | H | H | CH₃ | 50 | 25 | 66 | 43 | 184 |
| 10 | 1 | H | t-C₄H₉ | H | H | CH₃ | 23 | 4 | 10 | 3 | 40 |
| 11 | 3 | CH₃O | CH₃ | CH₃ | H | CH₃ | 7 at 10 lb/A | | 2 at 5 lb/A | | <12 |
| 12 | 1 | —CH₂CH₃OCH₂CH₂— | | H | H | CH₃ | 65 | 42 | 59 | 38 | 204 |
| Perfect Score | | | | | | | 96 | 96 | 96 | 96 | 384 |

In the total scores tabulated above, compound No. 5 appears to also be fairly effective. However, over a period of several months the weed control obtained with compound No. 6 appears to remain nearly complete, while with compound No. 5 there is a resurgence of weed growth. The reason becomes apparent when the two compounds are tested at lower application rates. Results obtained by comparing the two compounds at an application rate of ¼ lb per acre appear in Table IV. It is evident from these results that as the concentration of herbicide in the soil decreases, compound No. 5 becomes ineffective, while compound No. 6 continued to give complete control of a number of species.

TABLE IV

COMPARISON OF PRE-EMERGENT EFFECTIVENESS AT 1/4 LB. PER ACRE

| COMPOUND | NO. 5 | NO. 6 |
|---|---|---|
| Plant Species | | |
| Pigweed | 3 | 4 |
| Lambsquarter | 4 | 4 |
| Crabgrass | 1 | 4 |
| Downy Brome | 1 | 4 |
| Giant Foxtail | 1 | 4 |
| Nutsedge | 0 | 0 |
| Peanut | 0 | 0 |
| Cotton | 0 | 4 |
| Tomato | 3 | 4 |
| Sugar Beet | 0 | 4 |
| Wild Buckwheat | 0 | 4 |
| Wild Mustard | 2 | 4 |
| Cocklebur | 1 | 4 |
| Morning Glory | 1 | 4 |
| Soybean | 1 | 4 |
| Barnyard Grass | 1 | 4 |
| Green Foxtail | 1 | 4 |
| Alfalfa | 0 | 4 |
| Corn | 0 | 2 |
| Grain Sorghum | 1 | 3 |
| Shattercane | 1 | 4 |
| Wheat | 2 | 4 |
| Wheat | 2 | 4 |
| Wild Oats | 1 | 4 |
| Rice | 4 | 4 |

I claim:

1. The method of manufacturing a herbicidal composition consisting of the following steps, performed in sequence:

a. Chlorinating under oxidizing conditions an amine having the structural formula

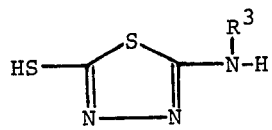

in which R³ may be methyl or ethyl to yield a corresponding sulfonyl chloride having the structural formula

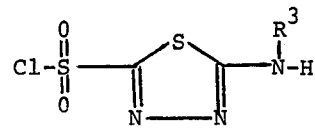

b. reacting the sulfonyl chloride produced in Step (a) with a secondary amine of the structural formula

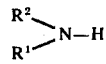

in which R¹ may be hydrogen or C₁ to C₄ lower alkyl and R² may be hydrogen or C₁ to C₄ lower alkyl or R¹ and R² together may form a morpholino ring with the nitrogen atom to yield a sulfonamide having the structural formula

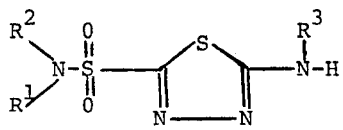

c. reacting the sulfonamide produced in step (b) with a carbamyl chloride or isocyanate having one of the structural formulae

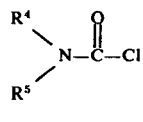

or R⁴NCO or reacting the amine substituent group with phosgene in an inert solvent, followed by reacting the resulting carbamyl chloride with an amine having the structural formula

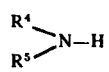

in which R⁴ may be hydrogen, methyl or ethyl and R⁵ may be hydrogen or C₁ to C₄ lower alkyl to yield a phytotoxic ureidothiadiazolesulfonamide having the structural formula

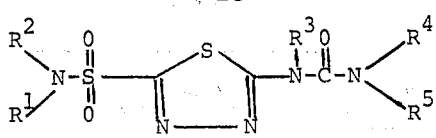

2. The method of manufacturing a herbicidal composition comprising the steps
   a. chlorinating under oxidizing conditions the amine having the structural formula

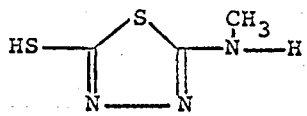

to yield the corresponding sulfonyl chloride having the structural formula

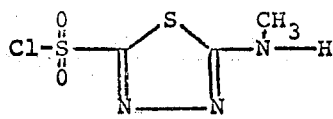

b. reacting the sulfonyl chloride produced in step (a) with a secondary amine having the structural formula

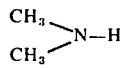

to yield a sulfonamide having the structural formula

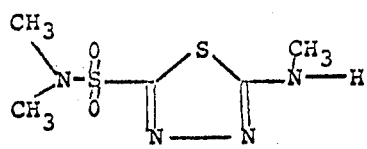

c. reacting the sulfonamide produced in step (b) with phosgene in an inert organic solvent followed by reacting the resulting carbamyl chloride with dimethylamine to yield a phytotoxic ureidothiadiazolesulfonamide having the structural formula

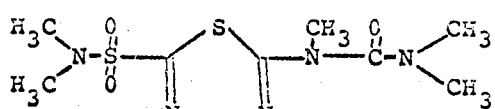

3. The sulfonyl chloride having the structural formula

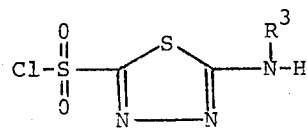

in which $R^3$ is methyl or ethyl.

* * * * *